US010697978B2

(12) United States Patent
Atzori et al.

(10) Patent No.: US 10,697,978 B2
(45) Date of Patent: Jun. 30, 2020

(54) METHOD FOR THE IN VITRO IDENTIFICATION OF DRUG-RESISTANT EPILEPSY

(71) Applicant: Universita' Degli Studi Di Cagliari, Cagliari (IT)

(72) Inventors: Luigi Atzori, Cagliari (IT); Federica Murgia, Cagliari (IT); Francesco Marrosu, Cagliari (IT); Francesco Del Carratore, Cagliari (IT)

(73) Assignee: Universita' Degli Studi de Cagliari, Cagliari (CA) (IT)

( * ) Notice: Subject to any disclaimer, the term of this patent is extended or adjusted under 35 U.S.C. 154(b) by 302 days.

(21) Appl. No.: 15/555,170

(22) PCT Filed: Mar. 2, 2016

(86) PCT No.: PCT/IB2016/051178
§ 371 (c)(1),
(2) Date: Sep. 1, 2017

(87) PCT Pub. No.: WO2016/139599
PCT Pub. Date: Sep. 9, 2016

(65) Prior Publication Data
US 2018/0052177 A1 Feb. 22, 2018

(30) Foreign Application Priority Data

Mar. 3, 2015 (IT) ................ M2015A0095

(51) Int. Cl.
| G01N 33/50 | (2006.01) |
| G01N 33/68 | (2006.01) |
| G01N 33/64 | (2006.01) |
| G01N 33/66 | (2006.01) |

(52) U.S. Cl.
CPC ......... *G01N 33/6896* (2013.01); *G01N 33/50* (2013.01); *G01N 33/64* (2013.01); *G01N 33/66* (2013.01); *G01N 33/6812* (2013.01); *G01N 2800/2857* (2013.01); *G01N 2800/52* (2013.01)

(58) Field of Classification Search
CPC .... G01N 33/6896; G01N 33/64; G01N 33/66; G01N 33/6812; G01N 2800/2857; G01N 2800/52
See application file for complete search history.

(56) References Cited

U.S. PATENT DOCUMENTS

2007/0042497 A1  2/2007  Campbell et al.

OTHER PUBLICATIONS

Pati Sandipan et al., *Pharmacoresistant Epilepsy: From Pathogenesis to Current and Emerging Therapies*, Cleveland Clinical J Med, 2010; vol. 77, No. 7, pp. 457-467.
*Epilepsy in the WHO European Region: Fostering Epilepsy Care in Europe*—http://www.ilae.org/visitors/documents/euroreport160510, Epilepsia, 2011, No. 52, vol. 1, pp. 187-188.
E. Perucca et al., *Comparative Effects of Rifabutin and Rifampicin on Hepatic Microsomal Enzyme Activity in Normal Subjects*. Eur J Clin Pharmacol. 1988; 34: 595-9.

(Continued)

*Primary Examiner* — Christopher Adam Hixson
(74) *Attorney, Agent, or Firm* — Workman Nydegger

(57) ABSTRACT

A method is provided for in vitro identification of drug-resistant epilepsy, which is based on the evaluation, in a biological sample, of the concentration of the metabolites 3-OH-butyrate, acetoacetate, choline, alanine, glutamate, scyllo-inositol, glucose, lactate and citrate.

4 Claims, 4 Drawing Sheets

(56) References Cited

OTHER PUBLICATIONS

Runa Kaddurah-Daouk et al., *Metabolomics: A Global Biochemical Approach to the Study of Central Nervous System Diseases*, Neuropsychopharmacology Review, 2009; vol. 34, pp. 173-186.

Mikhail Bogdanov et al., *Metabolomic Profiling to Develop Blood Biomarkers for Parkinson's Disease*, Brain 2008; vol. 131, pp. 389-396.

Ghaniah Hassan-Smith et al., *The Role of Metabolomics in Neurological Disease*, J Neuroimmunol 2012; vol. 248, pp. 48-52.

Helene Blasco et al., *1H-NMR-Based Metabolomic Profiling of CSF in Early Amyotrophic Lateral Sclerosis*, PLOS One 2010; vol. 5, Issue 10, e13223.

Alexandra J. Sinclair et al. *NMR-Based Metabolomic Analysis of Cerebrospinal Fluid and Serum in Neurological Diseases—A Diagnostic Tool?*, NMR Biomed. 2010, vol. 23, pp. 123-132.

Ignasi et al., *Alzheimer's Disease Beyond the Genomic Era: Nuclear Magnetic Resonance (NMR) Spectroscopy-Based Metabolomics*, J Cell Mol Med 2008, vol. 12, pp. 1477-1485.

Jeremy K. Nicholson et al., *Metabolic Phenotyping in Clinical and Surgical Environments*, Nature. 2012, vol. 491 pp. 384-392.

Patrick Kwan et al., *Definition of Drug Resistant Epilepsy: Consensus Proposal by the ad hoc Task Force of the ILAE Commission on Therapeutic Strategies*, Epilepsia, 2010, vol. 51, pp. 1069-1077.

Aalim M. Weljie et al., *Targeted Profiling: Quantitative Analysis of 1H NMR Metabolomics Data*, Anal Chem, 2006, vol. 78, pp. 4430-4442.

Maria Dahlina et al., *The Ketogenic Diet Influences the Levels of Excitatory and Inhibitory Amino Acids in the CSF in Children with Refractory Epilepsy*, Epilepsy Res., 2005, vol. 64, pp. 115-125.

Zhiyue, J. Wang et al. *In Vivo Measurement of Brain Metabolites Using Two-Dimensional Double-Quantum MR Spectroscopy Exploration of GABA Levels in a Ketogenic Diet*, Magnetic Resonance in Medicine, 2003, vol. 49, pp. 615-619.

John W. Gibbs et al., *Differential Epilepsy Associated Alterations in Postsynaptic GABA(A) Receptor Function in Dentate Granule and CA1 Neurons*, J Neurophysiol, 1997, vol. 77, pp. 1924-1938.

Amu R. Brooks-Kayal et al., *Selective Changes in Single Cell GABA(A) Receptor Subunit Expression and Function in Temporal Lobe Epilepsy*, Nat Med., 1998, vol. 4, pp. 1166-1172.

Akiva S. Cohen et al., *Dentate Granule Cell GABAA Receptors in Epileptic Hippocampus: Enhanced Synaptic Efficacy and Altered Pharmacology*, Euro J Neurosci, 2003, vol. 17, pp. 1607-1616.

Mussie G. Hadera et al. *Triheptanoin Partially Restores Levels of Tricarboxylic Acid Cycle Intermediates in the Mouse Pilocarpine Model of Epilepsy*, J Neurochem., 2013, vol. 29, pp. 107-119.

Olva B. Smeland et al., *Brain Mitochondrial Metabolic Dysfunction and Glutamate Level Reduction in the Pilocarpine Model of Temporal Lobe Epilepsy in Mice*, J Cereb Blood Flow Metab, 2013, vol. 33, pp. 1090-1097.

Edward R. Uhlemann et al., *Anticonvulsant Properties of the Ketogenic Diet in Mice*, J Pharmacol Exp Ther., 1972, vol. 180, pp. 231-238.

Ramakrishna Samala et al., *Anticonvulsant Profile of a Balanced Ketogenic Diet in Acute Mouse Seizure Models*, Epilepsy Res., 2008, vol. 81, pp. 119-127.

Melanie A. McNally et al., *Ketone Bodies in Epilepsy*, J Neurochem., 2012, vol. 121, pp. 28-35.

International Search Report and Written Opinion dated Jun. 23, 2016, issued in PCT Application PCT/IB2016/051178, filed Mar. 2, 2016.

O. Petroff et al., *High-Field Proton Magnetic Resonance Spectroscopy of Human Cerebrum Obtained During Surgery for Epilepsy*, Neurology, vol. 30, No. 9, Sep. 1989, pp. 1197-1202.

Xue-Bi Tian et al., *The Change in Cerebral Glucose Metabolism Generated by Electroacupuncture may predict the Outcome of Stimulation of the Anterior Nucleus Thalamus in Refractory Epilepsy*, Epilepsy and Behavior, vol. 29, No. 2, 2013, pp. 427-429.

R. Van Delft et al., *Blood Beta-Hydroxybutyrate Correlates Better with Seizure Reduction Due to Ketogenic Diet than do Ketones in the Urine*, Seizure, vol. 19, No. 1, Jan. 1, 2010, pp. 36-39.

V. O. Svystil'nyk, *Diagnostic and Prognostic Value of the Correlation of Brain Metabolites in Children with Epilepsy*, Likars'ka Sprava/ Ministerstvo Okhorony Zdorov'ia Ukrainy No. 1-2, Jan. 2005, pp. 75-80.

International Preliminary Report on Patentability dated Sep. 5, 2017, issued in PCT Application No. PCT/IB2016/051178, filed Mar. 2, 2016.

METHOD FOR THE IN VITRO IDENTIFICATION OF DRUG-RESISTANT EPILEPSY

BACKGROUND OF THE INVENTION

1. Field of the Invention

The present invention relates to a method for in vitro identification of drug-resistant epilepsy.

More in detail, the present invention relates to a method for in vitro identification of drug-resistant epilepsy, which is based on the evaluation, in a biological sample, of the concentration of the metabolites 3-OH-butyrate, acetoacetate, choline, alanine, glutamate, scyllo-inositol, glucose, lactate and citrate.

2. Present State of the Art

Drug resistance is a crucial problem in the treatment of patients suffering from epilepsy, which is one of the most frequent neurological diseases. Notwithstanding the introduction of new drugs developed for and aimed at the most critical points of the epileptogenic process, with multiple targets (the so-called "pleiotropic" mechanisms), one third of people suffering from epilepsy shows resistance to new and old antiepileptic drugs. Nowadays there is still a debate going on about the definition of "drug resistance in epilepsy"; however, drug resistance can be considered as an incomplete or absent response to drugs, which causes the onset of invalidating convulsions leading the involved individual to significant neuropsychiatric and social impairment, lowering quality of life and causing higher morbidity and higher risk of sudden death (1). The economic effect of this phenomenon is devastating: it has been estimated that 6,000,000 patients are suffering from active epilepsy in Europe, resulting in a yearly expense of 20 billion euros (2), plus disease-related familiar and social costs. It has nevertheless been observed that the solution to drug-resistant epilepsy might not be based on the use of drugs or medical devices (whether stimulators or based on epilepsy surgery), and this suggests the need for a strategy aimed at revealing, as early as possible, if a patient should be considered to be unfit for new pharmacological therapy attempts. The prognosis of a drug-resistant epileptic subject becomes evident only several years after the first treatment (3). Therefore, a crucial problem arises as concerns the devising of a therapeutic plan using a rational combination of two or more antiepileptic drugs in a drug-resistant patient. Very often, finding the clinical solution that provides the best therapeutic drug combination requires decades.

In light of the above, it is thus clear that a new kind of approach is needed which can ensure resource optimization both in economic terms and in terms of patient compliance, via a technique overcoming the problem of inter-individuality and making use of newly discovered predictive markers of responsiveness or not to therapy.

Metabolomics is an effective post-genomic research tool, which has been applied to many disciplines, including the study of human diseases, food checking, and vegetable physiology. Within the clinical frame, metabolomics has been recently used also for studying important neurologic diseases (4,5,6). The study of biofluids has been associated with the use of various analytical separation and revelation techniques, such as gas chromatography or liquid chromatography combined with mass spectrometry (GC-MS, LC-MS) and nuclear magnetic resonance (NMR); the latter has been the most used technique in neurology (7,8,9). The application of metabolomics represents an important advance towards the comprehension of metabolic components in the diagnosis, staging and grading of many diseases (10).

SUMMARY OF THE INVENTION

On the basis of the above considerations, the present inventors searched for possible markers for drug resistance in epilepsy in a population of subjects selected according to homogeneousness of the antiepileptic treatment. The metabolic profiles of a population of patients not responding to the therapy (NR), a population of patients responding to the therapy (R), and a population of healthy controls (C) were explored. The differences between such populations were highlighted and pointed out as possible tools for the diagnosis of drug resistance.

The present inventors found out that plasma of drug-resistant epileptic patients was characterized by higher levels of 3-OH-butyrate, acetoacetate, choline, alanine, glutamate and lower concentrations of glucose, lactate, citrate, scyllo-inositol than those of patients responding to the antiepileptic therapy. At first sight, the results of this study appear to be counter-intuitive, when compared with the traditional studies supporting the therapeutic efficacy of ketogenic diet. Actually, the ketone bodies produced after administration of the ketogenic diet have proved to be effective in controlling the crises (especially in epileptic children), even though the mechanism that stands at the basis of these effects is still partly unknown. Some studies suggest that the fundamental role played by ketone bodies consists in modulating the GABA-A receptor, thus exerting their antiepileptic effect. Specifically, increased levels of this inhibitory neurotransmitter have been observed in the cefaloarachidian fluid (CF) of patients subjected to ketogenic diet after survey by magnetic resonance spectroscopy (13, 14). However, experimental studies have suggested that chronic epilepsy causes a functional alteration of GABA receptor in the induction of neuronal inhibition, as demonstrated by the pilocarpine model of epilepsy (15-17). It is likely that an increased modulation mediated by the ketone bodies of GABA receptors might be poorly efficient in serious epileptic conditions.

The results of the present study can be interpreted by taking into account the general perturbation induced in cerebral metabolism by a condition of frequent crises, implying a serious reduction in energetic metabolites and a deep alteration of the homeostatic mechanisms that lead to changes in the physiology of the main bioenergetic players. Such critical aspects are expressed in the present study. In particular, alterations were observed in the glucose-lactate metabolism and in the tricarboxylic acids (TCA) cycle, which is deeply involved in the biochemical systems of cerebral metabolism. In fact, this study demonstrates that the serum levels of glucose and lactate decrease in subjects not responding to the antiepileptic treatment, compared with those who respond to the therapy, while in both groups the serum levels of the same metabolites are lower than those of a control group showing optimal use of the energetic resources. In particular, the reduced citrate concentration suggests a malfunctioning energetic mechanism of TCA, as disclosed by Smeland et al. 2013 in a model of induced convulsive activity (18, 19). These studies show a reduction in hippocampus citrate ($^{13}C$ enriched). It is interesting to note that the concentrations of citrate and glucose show a parallel decrease and a similar metabolic slope, just like lactate. In uncontrolled chronic convulsions, the cellular machinery may be forced to utilize other energetic resources, such as ketone bodies.

From this perspective, it seems likely that the increase in ketone bodies (as shown in the present study) is 1) an all-in-one spontaneous attempt to exploit an alternative energetic metabolism, and 2) an attempt to increase the antiepileptic effect, by dampening excitation and increasing inhibition. However, it seems possible that the non-enhancement of GABA-mediated inhibition due to increased ketone bodies is correlated with deep changes occurring in the sub-structural composition of GABA receptor. More specifically, a decrease in α1 sub-unit and an increase in α4 sub-unit have been described (16). The high variability in terms of composition of GABA receptor during epilepsy is supported by the interesting observation that sometimes ketogenic diet cannot protect the murine models of epilepsy induced by GABAr antagonists, whereas in the rat model a positive correlation has been shown with ketogenic diet (20, 21). Moreover, since it has been observed that the GABA levels do not change in murine models after administration of ketogenic diet, the hypothesis that a systemic reduction of epileptic crises can be obtained by simply increasing the level of such neurotransmitter appears to be simplistic. It follows, therefore, that it is necessary to further investigate the regional variations in the synthesis of GABA and of GABA shunt flow (22). Although the statistical power of this study can be improved by increasing the population, these preliminary results confirm that during drug-resistant epilepsy deep changes occur in cerebral metabolism, with modifications of natural processes, which are regulated in order to counter the general energy deficit.

This study demonstrates that, by using a small number of plasmatic metabolites, it is possible to grade a metabolic profile for drug-resistant patients. This selection will encourage physicians to adopt solutions that are not fully correlated to old/new antiepileptic drugs, as well as to place an accurate neurophysiologic study in view of more or less invasive surgical solutions (resective surgery, stimulators).

It is therefore a specific object of the present invention providing a method for in vitro identification of drug-resistant epilepsy, said method comprising or being consistent with the determination, in a plasma sample, of the concentration of each of the following metabolites: 3-OH-butyrate, acetoacetate, choline, alanine, glutamate, scyllo-inositol, glucose, lactate and citrate, wherein, in drug-resistant epilepsy, the concentration of each of the metabolites 3-OH-butyrate, acetoacetate, choline, alanine and glutamate is higher than the concentration of said metabolites in an epileptic subject responsive to antiepileptic therapy, and the concentration of each of the metabolites glucose, lactate, citrate and scyllo-inositol is less than the concentration of said metabolites in an epileptic subject responsive to antiepileptic therapy.

According to a preferred embodiment, the method of the present invention is based on the calculation of Mahalanobis distance. Said Mahalanobis distance is calculated on the basis of the concentrations of the above-mentioned metabolites for the drug-resistant epilepsy category.

A further object of the present invention is, therefore, the use of the metabolites 3-OH-butyrate, acetoacetate, choline, alanine, glutamate, scyllo-inositol, glucose, lactate and citrate (or of all the mentioned metabolites taken together), as biomarkers of drug-resistant epilepsy.

The present invention also relates to a method for in vitro identification of epilepsy, said method comprising or consisting of determining, in a plasma sample, the concentration of each of the following metabolites: acetone, acetoacetate, choline, scyllo-inositol, glutamate, lactate and citrate, wherein, in epilepsy, the concentration of each of the metabolites acetone, acetate, choline, scyllo-inositol is higher than the concentration of said metabolites in a healthy subject and the concentration of each of the metabolites lactate, citrate and glutamate is lower than the concentration of said metabolites in a healthy subject.

According to a preferred embodiment, the method of the present invention is based on the calculation of Mahalanobis distance. Said Mahalanobis distance is calculated on the basis of the concentrations of the above-mentioned metabolites for the epileptic patient category.

It is a further object of the present invention the use of metabolites acetone, acetoacetate, choline, scyllo-inositol, glutamate, lactate and citrate (or of all the mentioned metabolites taken together) as biomarkers of epilepsy.

Therefore, according to the present invention it is possible to discern among epileptic patient, epileptic patient responding to the therapy and drug-resistant patient by means of, for example, the method summarized below:

Extracting the above-mentioned metabolites from a plasma sample of the subjects belonging to two classes (e.g., Responder vs. Non Responder or Healthy vs Epileptic), e.g. by means of a chloroform/methanol solution;

Determining the metabolite concentration in the hydrophilic phase (e.g., by Nuclear Magnetic Resonance, but any technique leading to the determination of metabolite concentrations may be used as well);

Creating 2 matrices, one by class (subjects X metabolite concentration);

Calculating the covariance matrix ($S_c$) and the centroid associated to the matrix corresponding to the "class of interest" (i.e., the class to which the belonging or not is to be verified);

Calculating the Mahalanobis distance (MD) of each sample (of both matrices) by using the formula:

$$d_{i,C}^2 = (x_i - \bar{x}_C) \cdot S_C^{-1} \cdot (x_i - \bar{x}_C)^T$$

(see Example 1 for further details), a scalar (MD) will thus be associated to each sample; it is expected that the samples belonging to the class of interest have an MD which is, on average, lower than that of the samples not belonging to such a class;

by using this scalar, the ROC curve is then built in order to establish a threshold value and determine test performance;

for every new observation (every new patient whose belonging or not to the class of interest is to be determined) the first two steps are repeated and, once the metabolite concentrations have been obtained, the latters will be used for calculating the MD attributable to the new sample. If such a scalar turns out to be lower than the threshold value, then the sample will be considered as belonging to the class of interest.

For example, on the basis of the study disclosed in Example 1, for MD values below 14.85 the patient was classified as healthy, whereas for MD values greater than 14.85 the patient was classified as epileptic. Furthermore, for MD values below 15.65 the patient was classified as responsive to the antiepileptic therapy, whereas for MD values greater than 15.65 the patient was classified as drug-resistant epileptic.

BRIEF DESCRIPTION OF THE DRAWINGS

The present invention will now be described, by way of non limiting example, according to a preferred embodiment thereof with particular reference to the figures of the appended drawings, wherein.

DETAILED DESCRIPTION OF THE PREFERRED EMBODIMENTS

Figure 1:
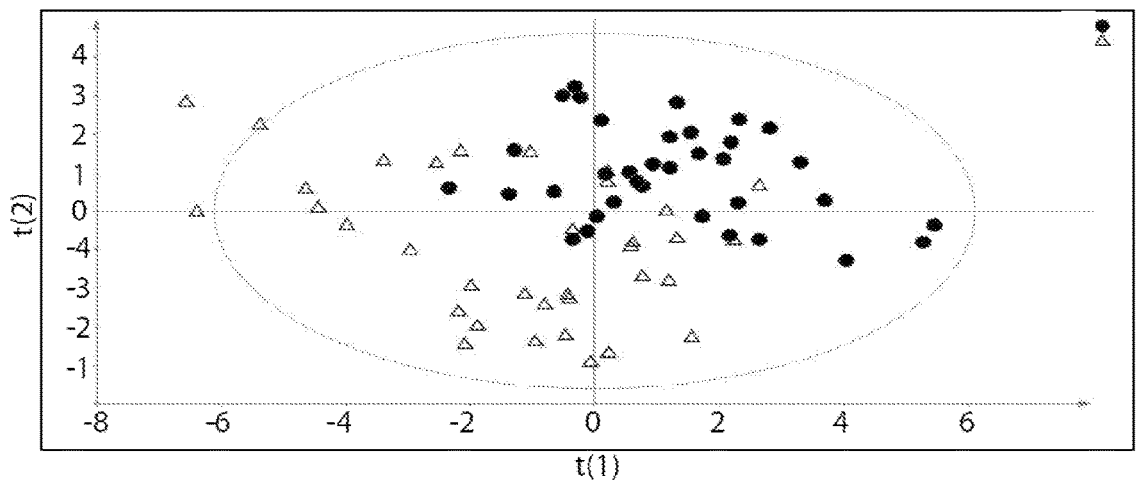
FIG. 1 shows PCA analysis of the samples enrolled in the study: in order to make the figure easier to read, the control samples (n=34 ●) and the epileptic patients (n=35 Δ) have been identified.

Example 1: Study on the Identification of Biomarkers of Drug-Resistant Epilepsy by a Metabolomic Approach Materials and Methods
Sample Collection The patients participating to the study, who suffered from pharmacologically well controlled partial epilepsy and drug-resistant partial epilepsy, were enrolled at the Centro Diagnosi e Trattamento Epilessia di Cagliari (Italia) and belonged to a group for which epilepsy had been diagnosed at least 4 years earlier. The main selection criteria for inclusion in the study were: i) a relative stability of the clinical characteristics connected with the interictal EEG activity, ii) resistance to the classical first- and second-line of antiepileptic drugs, evaluated every two months with respect to the controlled and stabilized group of epileptic subjects; iii) homogeneousness in the selection of the pharmacological treatment; iv) normal results of the neurological and psychiatric evaluations; v) lack of anomalies in the cerebral structure in a recent magnetic resonance. The controls were enrolled at the analysis laboratory of the clinical pathology department. Plasma samples were collected from fasting patients, and the groups were composed as follows: 1) no. 35 suffering from epilepsy and 2) no. 35 healthy controls (C). The first group was in turn formed by two subgroups: 1) no. 18 patients classified as responders (R) to pharmacological therapy and 2) no. 17 non responder patients (NR). The classification of the drug-resistant patients was made by following the described criteria (11). Six samples per each group were randomly selected for use as an external test set. The study was approved by the local ethical committee (NP/2013/438) and informed consent was obtained from each patient. Age and gender of each group were matched, as shown in Table 1.

TABLE 1

| Classes | Age (mean ± SD)/range | Gender (F/M) |
| --- | --- | --- |
| Controls (n = 34) | 45.35 ± 16.1$^t$/25-76 | 23/11 |
| Responders (n = 18) | 47.5 (±16.86) $^t$/27-80 | 11/7 |
| Non Responders (n = 17) | 52.17 (±9.57) $^t$/41-71 | 11/6 |

Therapy for pathologic patients consisted of carbamazepine, lamotrigine, topiramate, phenobarbital and benzodiazepines. Patients who took valproic acid and lacosamide were excluded in that the signals from those drugs disturbed the recognition of the metabolites present in the plasma NMR spectrum of such patients. Blood samples were centrifuged for 10 minutes at 1,700 g. Plasma was then separated, collected in 1 ml amounts, and preserved at −80° C. until the time of analysis.

Data Preparation and Acquisition

Plasma samples were unfrozen and centrifuged at 2,500 g for 10 min at 4° C. For the analysis, 800 µl of plasma were used, with the addition of 2,400 µl of a solution of 1:1 chloroform/methanol and 350 µl of distilled water. The samples were stirred for one minute and centrifuged for 30 minutes at 1,700 g at ambient temperature. Two phases were obtained: one hydrophilic and one hydrophobic. The former was concentrated overnight by speed-vacuum (Eppendorf concentrator plus, Eppendorf AG, Hamburg, Germany) and then re-suspended in 630 µl of $D_2O$ and 70 µl of 5.07 mM TSP (tetrasilylpropionic acid) (f.c.=50.7 µM). TSP was added and used as an internal reference for the chemical shifts of the signals of the spectrum obtained by NMR analysis. Six hundred and fifty microlitres of solution were transferred into the 5 mm NMR tube. The NMR experiment was acquired by using an NMR Varian UNITY INOVA 500 (Agilent Technologies, Inc., Santa Clara, Calif. 9505, USA) working at 499 MHz and equipped with a 5 mm triple resonance probe with z-axis pulsed field gradients and autosampler. The spectra were obtained by $^1$H-NMR monodimensional experiments at 300K by using a noesy-type sequence with suppression of the residual water signal and mixing time of 0.100 seconds. The spectra were recorded with 6,000.2 Hz spectral window, 1.5 sec acquisition time, 2 ms relaxation delay, 90° pulse and 9.2 µs, and a number of transients of 256. The signal was recorded by NMR as a FID (Free Induction Decay) and for each sample the following parameters were adopted: 64 k-dot zero-filling, 0.5 Hz line broadening. All spectra were manually phased and underwent a baseline correction and a shift of TSP (internal standard) to 0 ppm through the use of MestReNova software (version 8.1, Mestrelab Research S.L. Spain).

Data Processing and Multivariate Analysis

Each spectrum was divided into consecutive bins having an amplitude of 0.04 ppm. The investigated spectral area was between 0.52 and 8.8 ppm. The regions comprised between 4.64 and 5.2 ppm and between 5.28 and 6.72 ppm were excluded to avoid including areas in with the residual water signal and noise was present. In order to minimize the effect of the different concentrations of the plasma samples, the integrated area within each bin was normalized for the total area of the spectrum, which was set to 100. The final dataset consisted of a matrix of 159×70 values (variables× samples). In the matrix, the columns represent the normalized area of each bin (variables) and the rows represent the samples (subjects).

The multivariate statistical analysis was carried out by importing the matrix into SIMCA-P+ (version 13.0, Umetrics; Umea; Sweden). The NMR variables were scaled with Pareto in order to exalt the signals of all metabolites and reduce noise-induced information. The explorative initial analysis was made by studying the main components (PCA). Subsequently the Partial Least Square-Discriminant Analysis (PLS-DA) and the Orthogonal Partial Least Square-Discriminant Analysis (OPLS-DA) were used. PCA is important to explore the distribution of non-classified samples and to identify any possible outliers. PLS-DA and OPLS-DA are important to maximize the discrimination between samples belonging to different classes. In order to evaluate the quality of the models, variance and predictive capability (R2X, R2Y, Q2) were taken into account. Furthermore, for validation purposes, a permutation test (n=200) was carried out in order to test the degree of overfitting of the PLS-DA models. In this test the correlation coefficient between original Y and permutated Y is represented, by drawing a regression line between the values of R2 and cumulative Q2 and the intercept thereof. The values of the scores derived from each OPLS-DA model were subjected to CV-ANOVA in order to test the significance of the model, and validation was considered to be satisfactory for values of $p<0.05$. The most significant variables were extracted from the loadings plot of each model and the corresponding metabolites were identified and quantified by using Chenomx NMR Suite 7.1 (12). To this end, a customized library was created which included such metabolites, selected from a larger library of 300 metabolites, so as to be able to make comparisons of their relative concentrations among subjects belonging to different classes. Namely, such concentrations were used for conducting the multivariate analysis of variance (MANOVA) and then a series of univariated analysis tests (ANOVA) with SPSS 22 (SPSS Armonk N.Y.). In particular, for the multivariated tests, the Wilks' lambda test was carried out. This test is a direct measure of the portion of variance, considered as dependent variables, correlated to the independent variable (grouping variable or factor). If a wide portion of variance is correlated to the independent variable, then it is suggested a strong effect of the "group" factor due to the different mean values (in terms of metabolite concentrations) among the different groups. Last, the ROC curves were carried on by using the MATLAB software (MATLABR2012b.Ink) in order to test the specificity and sensitivity of the used method. The scalar employed for drawing the ROC curves is the Mahalanobis distance. This metric also allows considering the correlation among the variables.

Results

Figure 2:
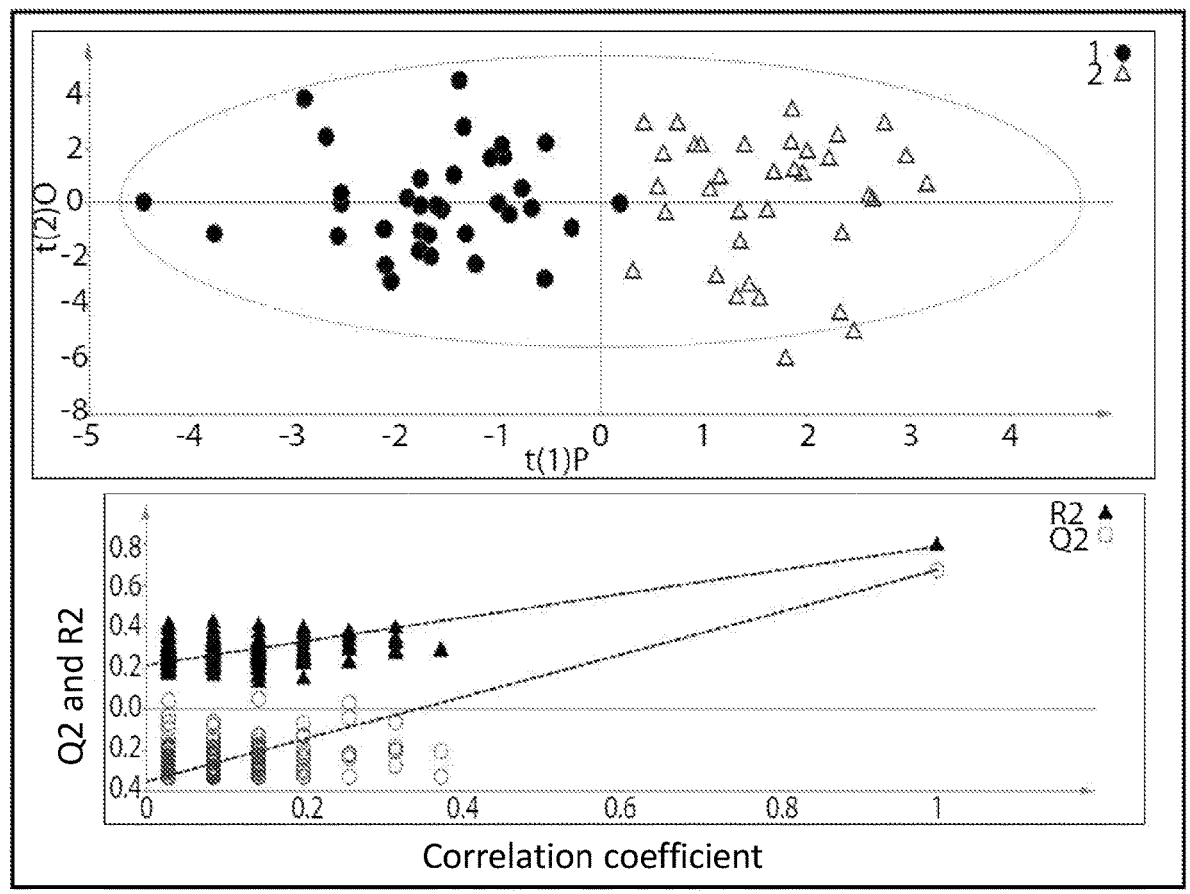
FIG. 2 shows the scores plot of the OPLS-DA multivariate model between healthy subjects (●) and epileptic patients (Δ): each dot represents a single plasma spectrum which position is determined by the contribution of the 159 variables. The image below shows the validation test (permutation test).

In order to evaluate the presence of clusters, a PCA analysis was carried out on the bins derived from the various spectra obtained by NMR (FIG. 1). Then an OPLS-DA model was made between the two groups: controls and epileptic patients (FIG. 2). In the model, one can note a different distribution of the two groups (p<0.001). The model parameters indicating variance (R2X and R2Y) and those indicating the predictive capability (Q2) were significantly high (R2X=0.571; R2Y=0.790; Q2=0.690).

Figure 3:
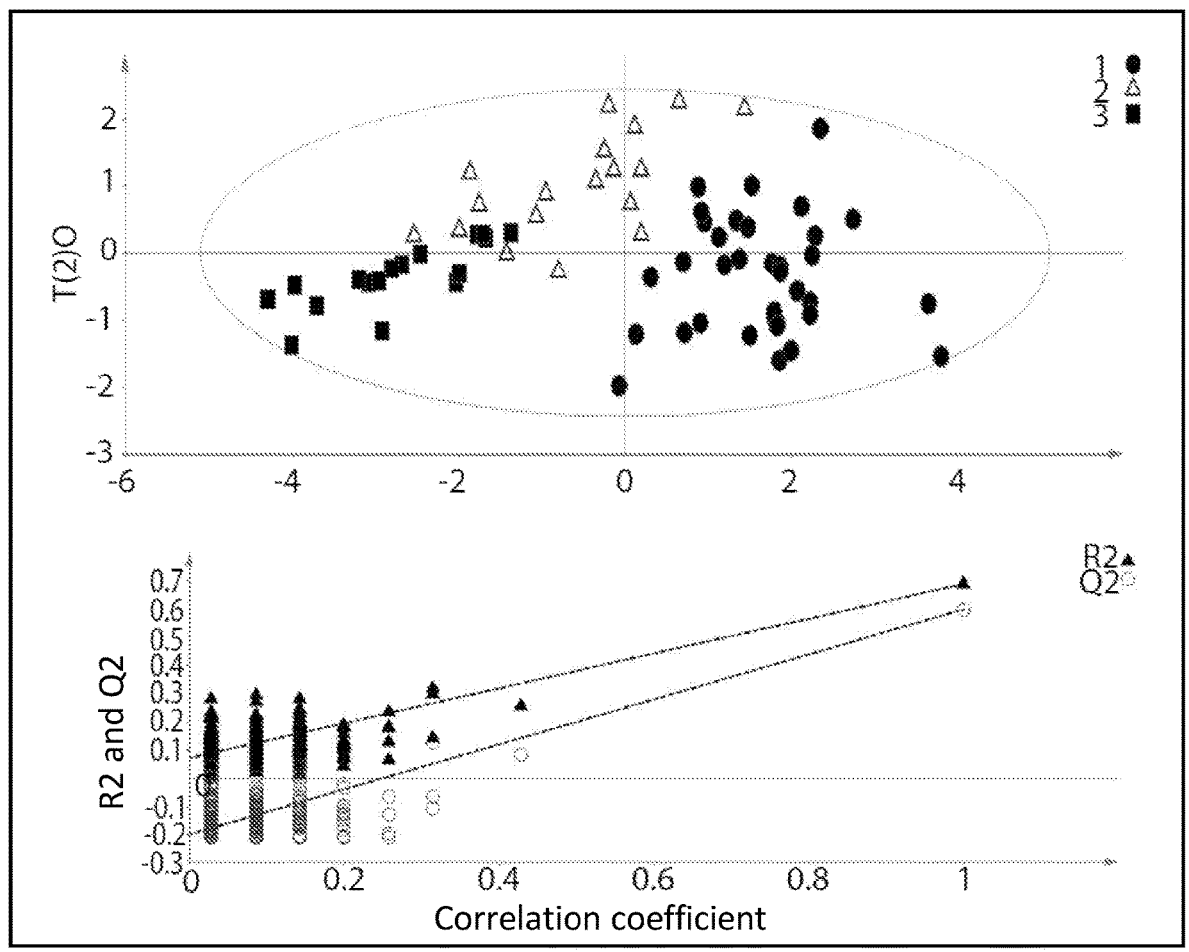
FIG. 3 shows that the profiles derived from healthy subjects (●), R patients (Δ) and NR patients (■) were significantly different; A) OPLS-DA model, B) statistical validation of the corresponding PLS-DA model by permutation test.

After observing a different metabolic profile between controls and epileptic patients, we studied the pathological group by verifying the possible differences between responders and non-responders to the therapy. Initially, the OPLS-DA of the three classes model: controls (C), responders (R) and non-responders (NR) was carried on, showing a significant p value (p<0.001). The statistical parameters for such a model were R2X=0.664, R2Y=0.615, Q2=0.477. Validation was carried out on the corresponding PLS-DA model by the permutation test (FIG. 3).

Figure 4:
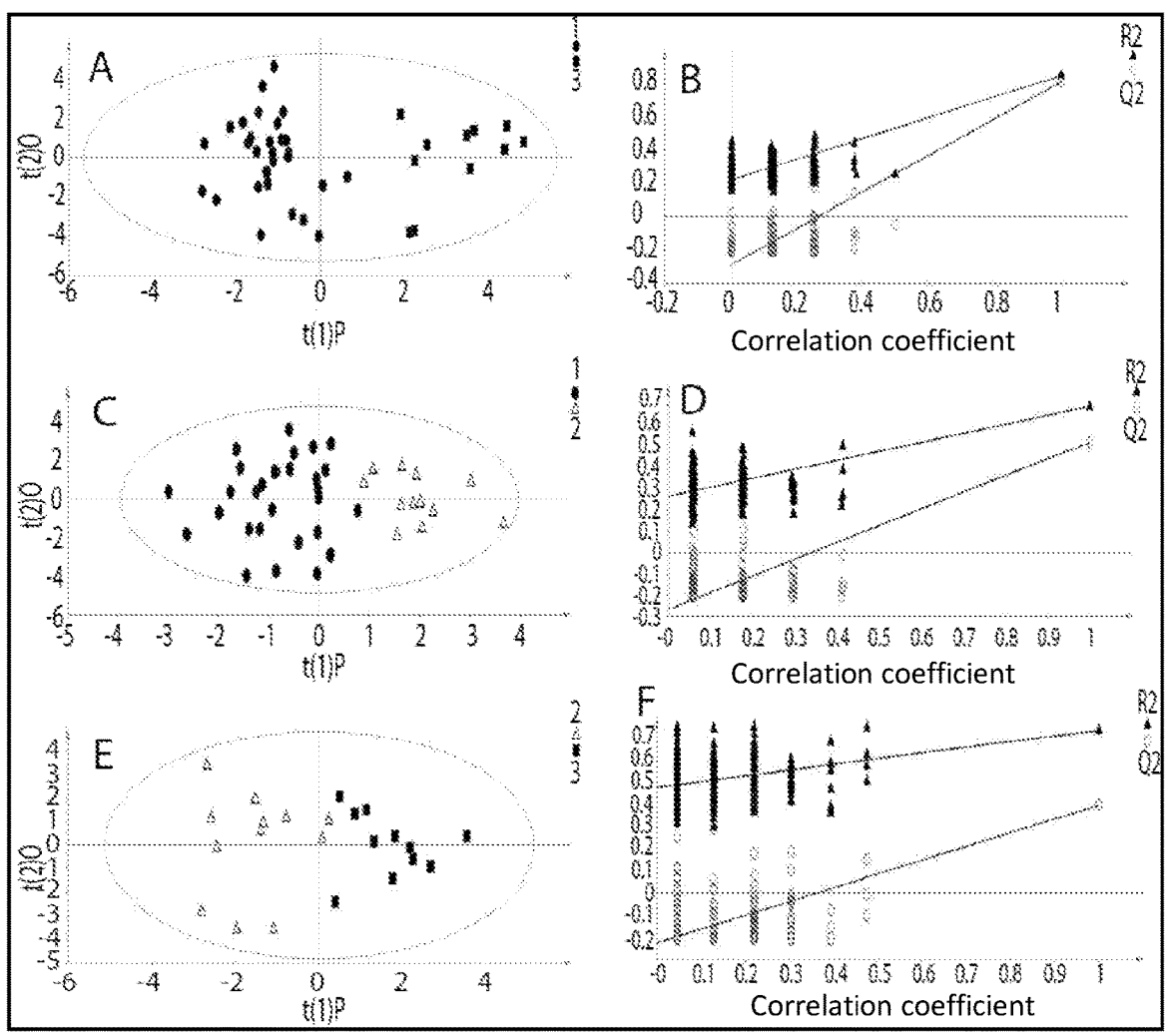
FIG. 4 shows A) that the plasma metabolic profile of healthy subjects (●) is different from that of NR patients (■), as shown by the OPLS-DA model. B) statistical validation of the corresponding PLS-DA model by permutation test. C) OPLS-DA between healthy subjects (●) and R patients (Δ) and D) corresponding permutation test, E) OPLS-DA model with R patients (Δ) and NR patients (■) with respective permutation test.

Each class was then individually compared with the others by OPLS-DA, and the results were validated by the permutation test of the respective PLS-DA models (FIG. 4 a-f).

A further validation test was carried out by using an external test set consisting of six samples belonging to each class. Such samples were projected into the model without providing any indication about the class they belonged to. The model returned a table wherein it associates a numerical value, from 0 to 1, with each observation, indicating its proximity to the classes of the model. The closer the value to 1, the higher the degree of belonging of that observation to the class. The average of such values for the subjects belonging to the different classes, shown as a percentage, is shown in Table 2.

TABLE 2

Mean and standard deviation (%) of the values of belonging of the subjects belonging to the different classes forming the external set.

| Models | Recognition rate ± S.D Controls | Recognition rate ± S.D Responders | Recognition rate ± S.D Non Responders |
|---|---|---|---|
| C vs NR | 0.88 ± 0.20 | | 0.73 ± 0.18 |
| C vs R | 0.75 ± 0.15 | 0.56 ± 0.22 | |
| R vs NR | | 0.58 ± 0.25 | 0.71 ± 0.28 |

The analysis between controls and non-responders showed positive statistical values, both in terms of variance and predictivity and p-value (R2X=0.495, R2y=0.853, Q2=0.807; P<0.001). Also the analysis performed between C and R showed significant statistical data: R2X=0.365, R2Y=0.694, Q2=0.580; p<0.001. The last analysis was conducted by comparing R and NR patients, and the statistical values turned out to be R2X=0.441, R2y=0.738, Q2=0.421; P=0.03.

Figure 5:
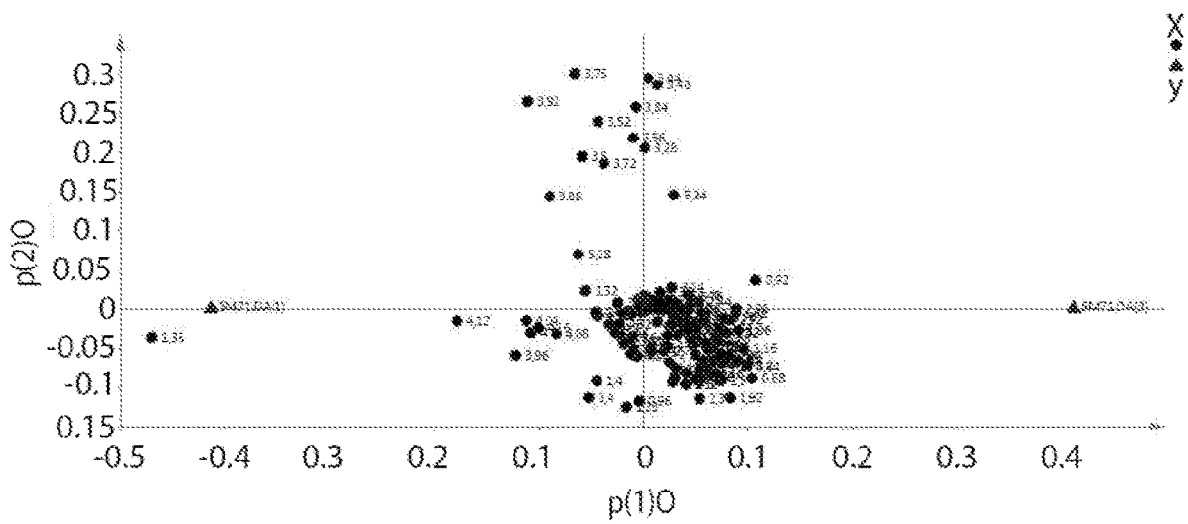
FIG. 5 shows loadings plot of the variables that discriminate model C vs. NR. Figure shows the distribution of the different variables generated by the spectra.

By using the loadings plot of each OPLS-DA model, it was possible to identify the variables discriminating between the classes. FIG. 5 shows the loadings plot of controls vs non responders, but also the loadings plot were studied for controls vs responders and of responders vs non-responders.

The metabolites corresponding to the discriminant variables were identified and quantified by using the Chenomx software. The metabolic discriminants were similar among the different groups. The plasma of the epileptic patients was characterized by higher levels of 3-OH-butyrate, 2-OH-valerate, 2-OH-butyrate, acetoacetate, acetone, acetate, choline, alanine, glutamate, scyllo-inositol (C<R<NR) and low concentrations of glucose, lactate, citrate in comparison with the controls (C>R>NR). Table 3 shows the different metabolic conditions.

TABLE 3

Different concentrations of the most important metabolites resulting from the analysis of the three groups.

| Metabolites | C | R | NR |
|---|---|---|---|
| CITRATE | +++ | ++ | + |
| LACTATE | +++ | ++ | + |
| GLUCOSE | +++ | ++ | + |
| GLUTAMATE | ++ | + | ++ |
| SCYLLO-INOSITOL | + | +++ | + |
| 2-OH-BUTYR/VALERATE | + | ++ | +++ |
| 3-OH-BUTYRATE | + | ++ | +++ |
| ACETOACETATE | + | ++ | +++ |
| ACETATE | + | ++ | +++ |
| ACETONE | + | ++ | +++ |
| ALANINE | + | + | ++ |
| CHOLINE | + | ++ | ++ |

The matrix containing the concentrations of the discriminant metabolites for each patient belonging to the three classes was analyzed with SPSS in order to obtain the analysis of variance with multivariated and univariated tests. Although the multivariated analysis showed that the discriminant metabolites for each mathematical model previously analyzed were the same, the univariated analysis showed some differences in terms of concentrations among the different classes. 2-OH-butyrate and 2-OH-valerate were not quantified because their signals overlapped in some spectral regions (triplet at 0.92 ppm). The multivariated tests were conducted on all groups by using the metabolite concentrations as variables. Wilks' lambda test showed a statistically significant difference in the metabolite concentrations in the three groups: $F(22, 114)=7.43$, $p<0.0005$; Wilk's $\Lambda=0.169$, partial $\eta 2=0.59$. The results were confirmed by other multivariated tests (Pillai's Trace, Hotelling's Trace, Roy's Largest Root). As a consequence of the results obtained from the multivariated tests among the groups, it was possible to study which metabolite changed significantly in terms of concentration among the three groups analyzed together. Univariated tests were used for determining the contribution of each metabolite. The results were as follows for p-value<0.001: acetate $F(2,67)=22$, acetoacetate $F(2,67)=14$, acetone $F(2,67)=15$, lactate $F(2,67)=12$, choline $F(2,67)=6$, p-value<0.05: citrate $F(2,67)=4$ and scyllo-inositol $F(2,67)=3.5$.

The Fisher's Least Significant Difference (LSD) test was used for exploring and comparing the mean values of the concentrations of the various metabolites among the various groups, analyzed two at a time, one against one. The results of the significantly varied metabolites are summarized in Table 4.

TABLE 4

Post-hoc Fisher's-LSD test of the discriminant metabolites. The table shows the p-value resulting from the comparison of the different groups

| Metabolite | C vs R | C vs NR | R vs NR |
|---|---|---|---|
| Acetate | p < 0.001 | p < 0.001 | ns |
| Acetoacetate | p < 0.01 | p < 0.001 | p < 0.05 |
| Acetone | p < 0.01 | p < 0.001 | p < 0.05 |
| Citrate | Ns | p < 0.05 | ns |
| Glucose | Ns | p < 0.05 | ns |
| Lactate | Ns | p < 0.001 | p < 0.001 |
| Scyllo-inositol | p < 0.05 | Ns | ns |

The statistical analyses carried out identify different metabolic profiles for the three groups. In particular, the group of pathological patients was characterized by higher levels of acetate, acetoacetate, acetone and scyllo-inositol (in particular in the resistant group) compared with the control groups, and, on the contrary, by lower levels of lactate, glucose and citrate. A particular characteristic of this study is the description of a fingerprint of NR patients, which was significantly different from that of R patients, due to an increased level of ketone bodies.

Unlike clinical chemistry, metabolomics typically involves different metabolites at the same time, rather than just one or two of them. Thus, in principle, metabolomics allows the researcher to evaluate multiple biomarkers within a single experiment.

The eleven metabolites identified by the multivariated analysis and their subsequent quantifications (it was not possible to quantify 2-OH-butyrate/valerate by the current method) were used for building two ROC curves: the first one concerning the controls-pathologicals analysis and the other one for the responders vs non responders analysis, for the purpose of determining the threshold value for the classification of the patients being studied. The building of the ROC curves also allowed us to establish the sensitivity and specificity level of our model.

Building the ROC curve requires the attribution of one scalar for each sample, taking into account the concentrations to it related of all metabolites involved. Such scalar was found in the Mahalanobis distance (MD) of each sample from the centroid of the group considered as a control group (controls in the "controls-pathologicals" analysis and responders in the responders-non responders analysis). MD takes into account the data correlation since it is calculated by using the inverse of the covariance matrix of the dataset of interest. MD is used in the multivariated analysis field for different purposes, such as: outliers detection, selection of calibration samples from a large set of measurements, pattern recognition, clustering techniques (such as the k-Nearest Neighbour method) and binary classification, such as the Linear Discriminant Analysis (LDA). Mahalanobis distance is calculated as follows:

$$d_{i,C}^2 = (x_i - \bar{x}_C) \cdot S_C^{-1} \cdot (x_i - \bar{x}_C)^T$$

where:

$x_i$ is the vector of the $i^{th}$ sample of size (1×n), where n is the number of metabolites taken into account and each element of the vector represents the concentration of one metabolite;

$\bar{x}_C$ is the centroid related to the group considered as the control group;

$S_C$ indicates the covariance matrix of the group considered as the control group;

T indicates the transposed matrix of the data.

Not all eleven metabolites turned out to be important for both the ROC curves. In fact, all possible combinations were evaluated, aiming at maximizing the AUC value and minimizing, as much as possible, the number of used metabolites.

Figure 6:
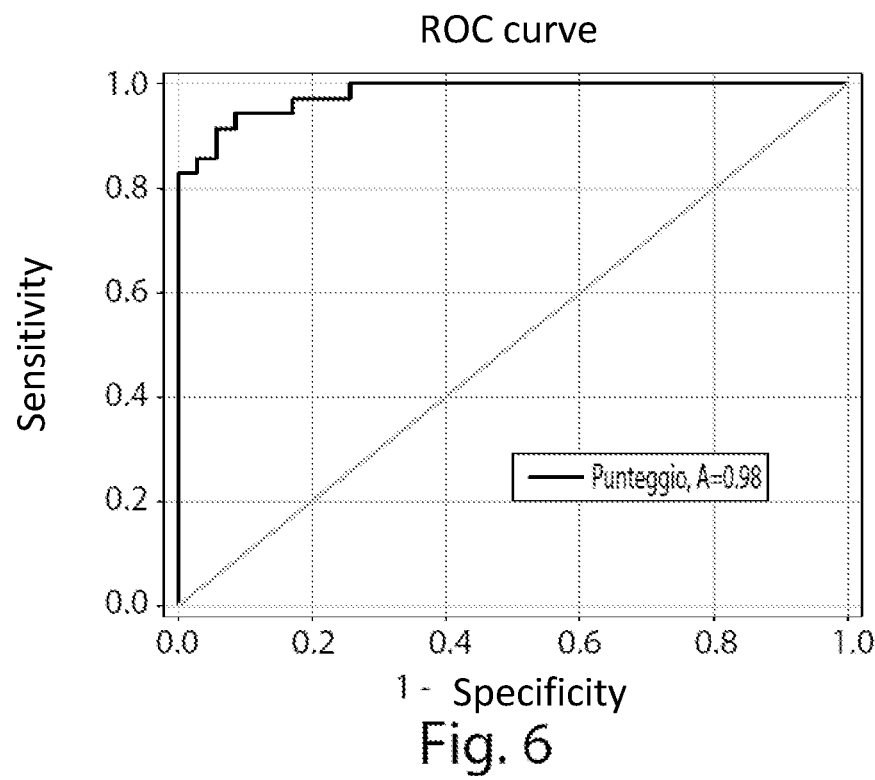
FIG. 6 shows the controls ROC curve vs epileptics.

For the controls vs epileptics analysis, the metabolites selected in accordance with the just above described procedure were: acetone, scyllo-inositol, choline, acetoacetate, citrate, glutamate and lactate. Below is shown the table with the statistical values of the respective ROC curve (Table 5 and FIG. 6).

TABLE 5

Statistical values of the Controls vs Epileptics ROC curve

| Test Variables | Score |
|---|---|
| ROC Curve Area | 0.9812 |
| Standard Error | 0.01174 |
| 95% Confidence Interval | 0.9582 to 1.000 |
| p Value | <0.0001 |

In consideration of the type of pathology and of its incidence on the population, wanting to privilege the capability of recognizing the highest number of diseased individuals (even at the risk of some false positives), it was decided to use 14.85 as a threshold value, so that for MD values<14.85 the patient will be classified as healthy, whereas for MD values>14.85 the patient will be classified as epileptic. For this threshold value, in Table 6 are shown the values and the C.I.'s relating to sensitivity and specificity.

TABLE 6

Sensitivity, specificity and C.I. built via the MD threshold value for Controls vs Epileptics

| MD Threshold | Sensitivity | C.I. 95% Sensitivity | Specificity | C.I. 95% Specificity |
|---|---|---|---|---|
| 14.85 | 0.9143 | 0.7694 to 0.9820 | 0.9429 | 0.8084 to 0.9930 |

Figure 7:
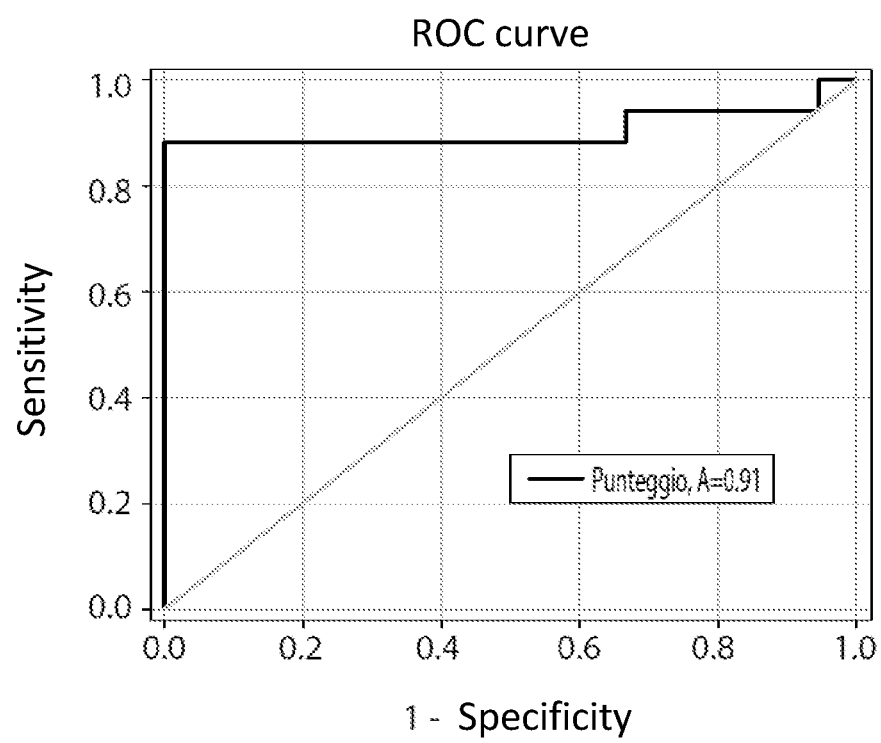
FIG. 7 shows the Responder ROC curve vs Non Responder.

For the responders vs non responders analysis, the metabolites selected in accordance with the just above-described procedure were: 3-hydroxybutyrate, acetoacetate, choline, citrate, glucose, glutamate, lactate, scyllo-inositol, alanine. Below is shown the table with the statistical values of the respective ROC curve (Table 7 and FIG. 7).

TABLE 7

Statistical values of the Responders vs Non Responders ROC curve

| Test Variables | Score |
|---|---|
| ROC Curve Area | 0.9052 |
| Standard Error | 0.0649 |
| 95% Confidence Interval | 0.7780 to 1.0000 |
| p Value | <0.0001 |

The optimal threshold value for classification between responders and non-responders turned out to be 15.65.

All samples having MD<15.65 will be considered responders, and vice versa for non-responders. The performances of a test built with this value are shown in Table 8.

TABLE 8

Sensitivity, specificity and C.I. built with a MD threshold value = 15.65 for Responders vs Non Responders

| MD Threshold | Sensitivity | C.I. 95% Sensitivity | Specificity | C.I. 95% Specificity |
|---|---|---|---|---|
| 15.65 | 0.8824 | 0.6356 to 0.9854 | 1 | 0.8147 to 1.000 |

Tables 9 and 10 show the relative concentrations of the metabolites in the Controls vs Epileptics and Responders vs Non Responders groups.

TABLE 9

| | C | E |
|---|---|---|
| acetoacetate | − | + |
| acetone | − | + |
| choline | − | + |
| scyllo-inositol | − | + |
| citrate | + | − |
| glutamate | + | − |
| lactate | + | − |

TABLE 10

| | R | NR |
|---|---|---|
| 3-OH-butyrate | − | + |
| Acetoacetate | − | + |
| Alanine | − | + |
| Choline | − | + |
| Glutamate | − | + |
| Citrate | + | − |
| Lactate | + | − |
| Glucose | + | − |
| Scyllo-inositol | + | − |

As above mentioned, building the ROC curve requires the attribution, for each sample, of a scalar that takes into account the concentrations to it related of all the considered metabolites. Said scalar was identified as the Mahalanobis distance (MD) of each sample from the centroid of the group considered as the control group (controls in the controls-pathologicals analysis and responders in the responders-non responders analysis). The MD takes into account data correlation since it is calculated by using the inverse of the covariance matrix of the dataset of interest. Below are shown the data relating to the analyses for the determination of the Mahalanobis distance and the ROC curves.

Centroid Data:

C vs E Group

| | mean | standard deviation |
|---|---|---|
| Acetate | 0.06127 | 0.018422517 |
| Acetone | 0.000833 | 0.00283865 |
| Choline | 0.01534 | 0.004287495 |
| Citrate | 0.123713 | 0.0471848 |
| Glutamate | 0.2971 | 0.08471355 |
| Lactate | 1.875823 | 0.459183903 |
| Scyllo-Inositol | 0.16189 | 0.143271086 |

R vs NR Group

| | mean | standard deviation |
|---|---|---|
| 3-Hydroxybutyrate | 0.116719 | 0.066634751 |
| Acetoacetate | 0.025767 | 0.01460576 |
| Alanine | 0.037347 | 0.019479835 |
| Choline | 0.019233 | 0.006178164 |
| Citrate | 0.101081 | 0.040207894 |
| Glucose | 1.815883 | 0.320329322 |
| Glutamate | 0.283747 | 0.081216603 |
| Lactate | 1.721594 | 0.523590109 |
| Scyllo-Inositol | 0.395219 | 0.523139345 |

Below are shown the data of the covariance matrix.

| C vs E Group | | | | | | | |
|---|---|---|---|---|---|---|---|
| | Acetate | Acetone | Choline | Citrate | Glutamate | Lactate | Scyllo-Inositol |
| Acetate | 3.39E−04 | −8.98E−06 | 1.50E−05 | 4.37E−04 | −1.29E−04 | 1.48E−03 | 0.00080971 |
| Acetone | −8.98E−06 | 8.06E−06 | 9.40E−08 | −1.69E−05 | −5.09E−05 | 0.000286 | −2.76E−05 |
| Choline | 1.50E−05 | 9.40E−08 | 1.84E−05 | 6.65E−05 | 6.31E−05 | 5.65E−04 | 0.00011595 |
| Citrate | 4.37E−04 | −1.69E−05 | 6.65E−05 | 0.002226 | 0.000834 | 0.004102 | 0.00170958 |
| Glutamate | −1.29E−04 | −5.09E−05 | 6.31E−05 | 0.000834 | 0.007176 | 0.010492 | 0.00020625 |
| Lactate | 1.48E−03 | 0.000286 | 5.65E−04 | 0.004102 | 0.010492 | 0.21085 | 0.01797237 |
| Scyllo-Inositol | 0.00081 | −2.76E−05 | 0.000116 | 0.00171 | 0.000206 | 0.017972 | 0.0205266 |

| R vs NR Group | | | | | |
|---|---|---|---|---|---|
| | 3-Hydroxybutyrate | Acetoacetate | Alanine | Choline | Citrate |
| 3-Hydroxybutyrate | 0.00444019 | 0.000284555 | 5.53E−04 | 6.43E−05 | 0.001686018 |
| Acetoacetate | 0.000284555 | 0.000213328 | 1.71E−04 | −5.06E−05 | 0.00021433 |
| Alanine | 5.53E−04 | 1.71E−04 | 3.79E−04 | 9.25E−06 | 4.34E−04 |
| Choline | 6.43E−05 | −5.06E−05 | 9.25E−06 | 3.82E−05 | 6.06E−06 |
| Citrate | 0.001686018 | 0.00021433 | 4.34E−04 | 6.06E−06 | 0.001616675 |
| Glucose | 0.012012092 | 2.40E−03 | 2.77E−03 | −0.00019112 | 3.42E−03 |
| Glutamate | 0.001033072 | 0.000603573 | 0.000726516 | −8.81E−06 | 0.000607804 |
| Lactate | 0.008136587 | −0.001134928 | 0.000217601 | 0.00059672 | 0.006912947 |
| Scyllo-Inositol | 0.007199634 | −4.96E−04 | 1.27E−03 | −3.45E−04 | 0.006509533 |

| | Glucose | Glutamate | Lactate | Scyllo-Inositol |
|---|---|---|---|---|
| 3-Hydroxybutyrate | 0.012012092 | 0.001033072 | 0.008136587 | 0.007199634 |
| Acetoacetate | 2.40E−03 | 0.000603573 | −0.001134928 | −4.96E−04 |
| Alanine | 2.77E−03 | 0.000726516 | 0.000217601 | 1.27E−03 |
| Choline | −0.000191116 | −8.81E−06 | 0.00059672 | −3.45E−04 |
| Citrate | 3.42E−03 | 0.000607804 | 0.006912947 | 0.006509533 |
| Glucose | 0.102610874 | 0.009875324 | −0.021362701 | 0.037400275 |
| Glutamate | 0.009875324 | 0.006596137 | −0.019281218 | −0.016779471 |
| Lactate | −0.021362701 | −0.019281218 | 0.274146603 | 0.131526007 |
| Scyllo-Inositol | 0.037400275 | −0.016779471 | 0.131526007 | 0.273674774 |

BIBLIOGRAPHY

1) Pati S. and Alexopoulos A V, Pharmacoresistant epilepsy: From pathogenesis to current and emerging therapies, Cleve Clin J Med 2010; 77:7457-467.
2) Epilepsy in the WHO European Region: Fostering Epilepsy Care in Europe—http://www.ilae.org/visitors/documents/euroreport160510.pdf
3) Perucca E, Grimaldi R, Frigo G M, Sardi A, Mönig H, and Ohnhaus E E. Comparative effects of rifabutin and rifampicin on hepatic microsomal enzyme activity in normal subjects. Eur J Clin Pharmacol. 1988; 34: 595-9.
4) Kaddurah-Daouk R. and Krishnan K R. Metabolomics: A Global Biochemical Approach to the Study of Central Nervous System Diseases Neuropsychopharmacology 2009; 34: 173-186.
5) Bogdanov M, Matson W R, Wang L, Matson T, Saunders-Pullman R, Bressman S S and Flint Beal M. Metabolomic profiling to develop blood biomarkers for Parkinson's disease, Brain 2008; 131:389-396.
6) Hassan-Smith G, Wallace G R, Douglas M R, Sinclair A J, The role of metabolomics in neurological disease, J Neuroimmunol 2012; 248: 48-52.
7) Blasco H, Corcia P, Moreau C, Veau S, Fournier C, Vourch P, Emond P, Gordon P, Pradat P F, Praline J, Devos D, Lydie Nadal-Desbarats, Christian R. Andres, 1H-NMR-Based Metabolomic Profiling of CSF in Early Amyotrophic Lateral Sclerosis, Plos One 2010; 5: e13223.
8) Sinclair A J, Viantc M R, Balld A K, Burdona M A, Walkerb E A, Stewartb P M, Rauza S and Younge S P, NMR-based metabolomic analysis of cerebrospinal fluid and serum in neurological diseases—a diagnostic tool? NMR Biomed. 2010; 23:123-132.
9) Barba I, Fernandez-Montesinos R, Garcia-Dorado D, Pozo D, Alzheimer's disease beyond the genomic era: nuclear magnetic resonance (NMR) spectroscopy-based metabolomics, J Cell Mol Med 2008; 12: 1477-1485.
10) Nicholson J K, Holmes E, Kinross J M, Darzi A W, Takats Z, Lindon J C. Metabolic phenotyping in clinical and surgical environments, Nature. 2012; 491:384-92.
11) Kwan P, Arzimanoglou A, Berg A T, Brodie M J, Allen Hauser W, Mathern G, Moshé S L, Perucca E, Wiebe S, French J, Definition of drug resistant epilepsy: Consensus proposal by the ad hoc Task Force of the ILAE Commission on Therapeutic Strategies, Epilepsia. 2010; 51:1069-77.
12) Weljie A M, Newton J, Mercier P, Carlosn E, Slupsky C M, Targeted profiling: quantitative analysis of 1H NMR metabolomics data, Anal Chem 2006; 78:4430-42.
13) Dahlina M, Elfving A, Ungerstedtb U, Amark P, The ketogenic diet influences the levels of excitatory and inhibitory aminoacids in the CSF in children with refractory epilepsy, Epilepsy Res 2005; 64 115-125.
14) Wang Z J, Bergqvist C, Hunter J V, Jin D, Wang D J, Wehrli S, and R A. Zimmerman, In Vivo Measurement of Brain Metabolites Using Two-Dimensional Double-Quantum MR Spectroscopy Exploration of GABA Levels in a Ketogenic Diet, Magn Reson Med 2003; 49:615-619.
15) Gibbs J W, Shumate M D, Coulter D A, Differential epilepsy associated alterations in postsynaptic GABA(A) Receptor function in dentate granule and CA1 neurons, J Neurophysiol 1997; 77:1924-1938.
16) Brooks-Kayal A R, Shumate M D, Jin H, Rikhter T Y, Coulter D A, Selective changes in single cell GABA(A) Receptor subunit expression and function in temporal lobe epilepsy, Nat Med 1998; 4:1166-1172.
17) Cohen A S, Lin D D, Quirk G L and Coulter D A, Dentate granule cell GABAA receptors in epileptic hippocampus: enhanced synaptic efficacy and altered pharmacology, Euro J Neurosci 2003; 17, 1607-1616.
18) Hadera M G, Smeland O B, McDonald T S, Tan K N, Sonnewald U, Borges K, Triheptanoin partially restores levels of tricarboxylic acid cycle intermediates in the mouse pilocarpine model of epilepsy, J Neurochem 2013; 1111/jnc.12610
19) Smeland O B, Hadera M G, McDonald T S, Sonnewald U and Borges K, Brain mitochondrial metabolic dysfunction and glutamate level reduction in the pilocarpine model of temporal lobe epilepsy in mice, J Cereb Blood Flow Metab 2013; 33, 1090-1097.
20) Uhlemann E R and Neims A H, Anticonvulsant properties of the ketogenic diet in mice, J Pharmacol Exp Ther. 1972; 180: 231-238.
21) Samala R, Willis S, Borges K, Anticonvulsant profile of a balanced ketogenic diet in acute mouse seizure models, Epilepsy Res. 2008; 81:119-27.
22) McNally M A, Hartman A L, Ketone bodies in epilepsy. J Neurochem 2012; 121:28-35.

The invention claimed is:
1. A method for in vitro identification of antiepileptic-therapy-resistant epilepsy from a plasma sample, said method comprising:
   subjecting the plasma sample to extraction by means of a chloroform/methanol solution and water in order to obtain a lipohilic phase and a hydrophilic phase;
   separating the hydrophilic phase and determining a concentration of each of the following metabolites: 3-OH-butyrate, acetoacetate, choline, alanine, glutamate, scyllo-inositol, glucose, lactate, and citrate;
   creating a first matrix comprising metabolite concentration data for antiepileptic-therapy-resistant epileptic subjects and metabolite concentration data for antiepileptic-therapy-responsive epileptic subjects,
   calculating a covariance matrix and a centroid associated with a class of interest within the first matrix;
   calculating a Mahalanobis Distance (MD) for each sample of the first matrix using the formula:

$$d_{i,C}^2 = (x_i - \bar{x}_C) \cdot S_C^{-1} \cdot (x_i - \bar{x}_C)^T,$$

where $x_i$ is the vector of the $i^{th}$ sample of size (1×n),
   where n is a number of metabolites taken into account and each element of the vector represents a concentration of one metabolite,
   where $\bar{x}_C$ is the centroid associated with a control group, and
   where $S_C$ indicates the covariance matrix of the control group;
   associating a scalar MD value with each sample in the first matrix;
   using these scalar MD values, building a Receiver Operating Characteristic (ROC) curve to establish a threshold value for antiepileptic therapy resistant epilepsy; and
   determining a plasma sample scalar MD based on the determined concentration of each metabolite within the plasma sample; and
   based on the threshold value and the plasma sample scalar MD, determining whether the plasma sample is associated with an antiepileptic-therapy-responsive epileptic subject,
   wherein, in an antiepileptic-therapy-resistant epileptic subject, the concentration of each of the metabolites 3-OH-butyrate, acetoacetate, choline, alanine, and glutamate is greater than the concentration of said metabolites in an antiepileptic therapy responsive epileptic subject, and
   wherein the concentration of each of the metabolites glucose, lactate, citrate, and scyllo-inositol is less than the concentration of said metabolites in an antiepileptic therapy responsive epileptic subject.

2. A method for in vitro identification of epilepsy in plasma samples, said method comprising:
   subjecting the plasma sample to extraction by means of a chloroform/methanol solution and water in order to obtain a lipophilic phase and a hydrophilic phase;
   separating the hydrophilic phase and determining a concentration of each of the following metabolites: acetone, acetate, choline, scyllo-inositol, glutamate, lactate, and citrate;
   creating a first matrix comprising metabolite concentration data for healthy, non-epileptic subjects and metabolite concentration data for epileptic subjects,
   calculating a covariance matrix and a centroid associated with a class of interest within the first matrix;
   calculating a Mahalanobis Distance (MD) for each sample of the first matrix using the formula:

$$d_{i,C}^2 = (x_i - \bar{x}_C) \cdot S_C^{-1} \cdot (x_i - \bar{x}_C)^T,$$

where $x_i$ is the vector of the $i^{th}$ sample of size (1×n),
   where n is a number of metabolites taken into account and each element of the vector represents a concentration of one metabolite,
   where $\bar{x}_C$ is the centroid associated with a control group, and
   where $S_C$ indicates the covariance matrix of the control group;
   associating a scalar MD value with each sample in the first matrix;
   using these scalar MD values, building a Receiver Operating Characteristic (ROC) curve to establish a threshold value for epilepsy; and
   determining a plasma sample scalar MD based on the determined concentration of each metabolite within the plasma sample; and
   based on the threshold value and the plasma sample scalar MD, determining whether the plasma sample is associated with an epileptic subject,
   wherein, in an epileptic subject, the concentration of each of the metabolites acetone, acetate, choline, scyllo-inositol is greater than the concentration of said metabolites in a healthy, non-epileptic subject, and the concentration of each of the metabolites lactate, citrate, and glutamate is less than the concentration of these-said metabolites in a healthy, non-epileptic subject.

3. A method for in vitro identification of epilepsy, comprising:
  receiving concentrations of a plurality of metabolites measured from a plasma sample of a subject, the plurality of metabolites comprising one or more of: 3-OH-butyrate, acetate, acetoacetate, acetone, choline, alanine, glutamate, scyllo-inositol, glucose, lactate, and citrate;
  generating a first vector $x_1$ of size (1×n),
    where n is a number of metabolites in a first subset of the plurality of metabolites comprising one or more of: acetone, acetate, choline, scyllo-inositol, glutamate, lactate, and citrate, and
    where each element of the vector $x_1$ represents a corresponding metabolite concentration for each metabolite in the first subset;
  calculating a first scalar for the subject plasma sample using the formula:
  $$d_{1,C}^2 = (x_1 - \bar{x}_C) \cdot S_C^{-1} \cdot (x_1 - \bar{x}_C)^T,$$
    where $\bar{x}_C$ is a centroid corresponding to a control group of healthy, non-epileptic subjects, and
    where $S_C$ corresponds to a covariance matrix of the control group; and
  determining whether the subject has epilepsy based on the first scalar, wherein if the first scalar is greater than a first threshold value, then the subject is epileptic, and wherein if the first scalar is less than the first threshold value, then the subject is non-epileptic.

4. The method according to claim 3, wherein the first scalar is greater than the first threshold value, and the method further comprises determining whether the epileptic subject is an antiepileptic-therapy-responsive epileptic subject, wherein said determining comprises:
  generating a second vector $x_2$ of size (1×m),
    where m is a number of metabolites in a second subset of the plurality of metabolites comprising one or more of: 3-OH-butyrate, acetoacetate, choline, alanine, glutamate, scyllo-inositol, glucose, lactate, and citrate, and
    where each element of the vector $x_2$ represents a corresponding metabolite concentration for each metabolite in the second subset;
  calculating a second scalar for the subject plasma sample using the formula:
  $$d_{2,C}^2 = (x_2 - \bar{x}_C) \cdot S_C^{-1} \cdot (x_2 - \bar{x}_C)^T$$
    where $\bar{x}_C$ is a centroid corresponding to a second control group of antiepileptic-therapy-responsive epileptic subject, and
    where $S_C$ corresponds to a covariance matrix of the second control group; and
  determining whether the epileptic subject is an antiepileptic-therapy-responsive epileptic subject based on the second scalar, wherein if the second scalar is greater than a second threshold value, then the epileptic subject is an antiepileptic-therapy-resistant epileptic subject, and wherein if the second scalar is less than the second threshold value, then the subject is an antiepileptic-therapy-responsive epileptic subject.

* * * * *